(12) United States Patent
Boucherie

(10) Patent No.: US 8,071,001 B2
(45) Date of Patent: Dec. 6, 2011

(54) METHOD AND DEVICE FOR MANUFACTURING PLUNGERS FOR MEDICAL SYRINGES, PLUNGERS OBTAINED THEREBY, AS WELL AS SYRINGE FOR MEDICAL PURPOSES

(75) Inventor: Bart Gerard Boucherie, Izegem (BE)

(73) Assignee: Boutech, Naamloze Vennotschap, Izegem (BE)

( * ) Notice: Subject to any disclaimer, the term of this patent is extended or adjusted under 35 U.S.C. 154(b) by 1285 days.

(21) Appl. No.: 10/530,351

(22) PCT Filed: Sep. 24, 2003

(86) PCT No.: PCT/BE03/00157
§ 371 (c)(1),
(2), (4) Date: Apr. 6, 2005

(87) PCT Pub. No.: WO2004/035289
PCT Pub. Date: Apr. 29, 2004

(65) Prior Publication Data
US 2006/0089602 A1  Apr. 27, 2006

Related U.S. Application Data

(60) Provisional application No. 60/448,899, filed on Feb. 24, 2003.

(30) Foreign Application Priority Data

Oct. 14, 2002  (BE) .................................. 2002/0592
Feb. 14, 2003  (BE) .................................. 2003/0103

(51) Int. Cl.
*B29C 45/16*  (2006.01)

(52) U.S. Cl. ...................................... 264/255; 264/328.8
(58) Field of Classification Search .................... 264/255
See application file for complete search history.

(56) References Cited

U.S. PATENT DOCUMENTS 3,659,749 A * 5/1972 Schwartz ....................... 222/129
4,861,335 A * 8/1989 Reynolds ......................... 604/88
5,030,406 A   7/1991 Sorensen
(Continued)

FOREIGN PATENT DOCUMENTS

CA  2189449  11/1995
(Continued)

OTHER PUBLICATIONS

Translation of JP 2001-259031 (related to document to WO 01/70311).*

*Primary Examiner* — Monica A Huson
(74) *Attorney, Agent, or Firm* — Bacon & Thomas, PLLC

(57) ABSTRACT

Method for manufacturing plungers for medical syringes, whereby such a plunger (3) consists of at least two parts, namely a longitudinal plunger body (4) made of plastic and a piston body (5) provided at the front end of the plunger body (4) which consists of a plastic which is softer than the plastic of the plunger body (4), characterised in that such a plunger (3), or at least a part (36) thereof, is formed by first manufacturing the piston body (5) and then the plunger body (4), or at least a part (37) of this plunger body (4), by means of injection moulding, whereby the plunger body (4), or the above-mentioned part (37) thereof, is injected against the piston body (5).

15 Claims, 7 Drawing Sheets

U.S. PATENT DOCUMENTS 5,094,148 A 3/1992 Haber et al.
5,782,803 A 7/1998 Jentzen

FOREIGN PATENT DOCUMENTS

| | | |
|---|---|---|
| CN | 2507470 Y | 8/2002 |
| EP | 0 354 368 A2 | 2/1990 |
| EP | 0 375 778 A1 | 7/1990 |
| EP | 1 099 449 A1 | 5/2001 |
| JP | 58-67265 | 4/1983 |
| JP | 64-85665 | 3/1989 |
| JP | 5-131029 | 5/1993 |
| JP | 8-276462 | 10/1996 |
| JP | 08-280804 | 10/1996 |
| JP | 11-268077 | 10/1999 |
| JP | 2001-137338 | 5/2001 |
| JP | 2001-259031 | 9/2001 |
| JP | 2001-259032 | 9/2001 |
| JP | 2002-210010 | 7/2002 |
| WO | 79/01111 | 12/1979 |
| WO | 95/30446 | 11/1995 |
| WO | 01/70311 A1 | 9/2001 |
| WO | WO 01/70311 A1 | 9/2001 |

* cited by examiner

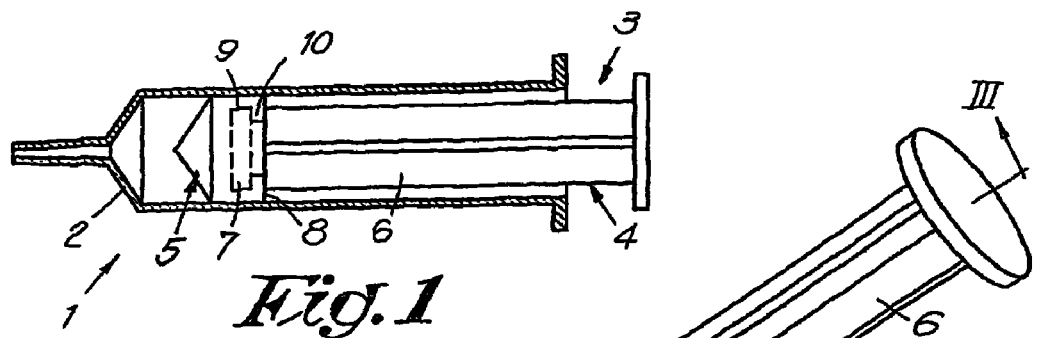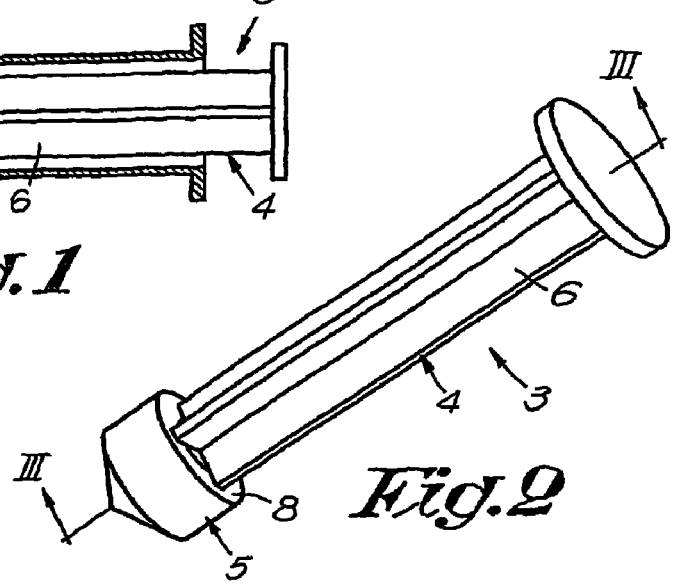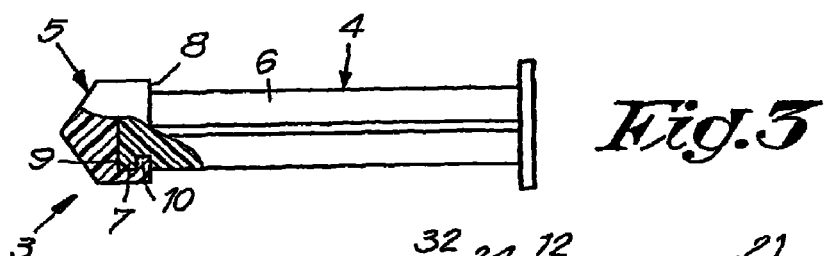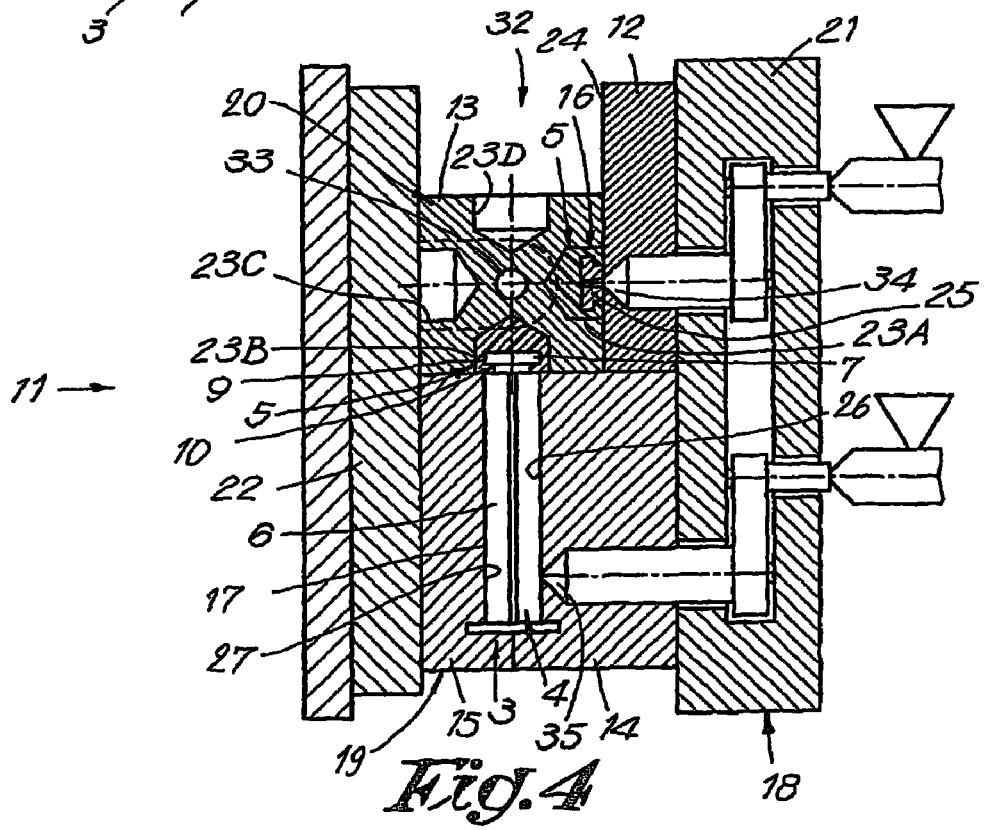

METHOD AND DEVICE FOR MANUFACTURING PLUNGERS FOR MEDICAL SYRINGES, PLUNGERS OBTAINED THEREBY, AS WELL AS SYRINGE FOR MEDICAL PURPOSES

The present invention concerns methods for manufacturing plungers for medical syringes, as well as devices applying such method and plungers obtained according to said method. Further, it also concerns different embodiments of syringes, in particular syringes with special embodiments of plungers.

In particular, the invention concerns a method for manufacturing such plungers out of plastic.

By syringes should be understood in this case all recipients provided with a piston or plunger with which liquid can be sucked up in the recipient and/or can be pressed out of the recipient. Examples thereof are injection syringes and dose syringes.

The above-mentioned plungers, which are designed to be pushed in a slidable manner in a usually cylindrical recipient, as is known consist of a longitudinal plunger body upon which is fixed a piston body at the front in the shape of a head. The plunger body is usually made of a relatively hard plastic, whereas the piston body is made of a softer material which guarantees a good sealing against the cylinder wall of the syringe.

The above-mentioned parts, the plunger body on the one hand and the piston body on the other hand, are traditionally made entirely separately, to be subsequently assembled, either manually or by means of an assembly machine.

The two aforesaid parts of the known plungers are traditionally attached to each other by means of a sort of snap-in system, in particular by means of collars meshing behind one another, such that the piston body can be pressed down on the far end of the plunger body.

As, according to the known technique, the two parts of a plunger are manufactured separately and have to be subsequently assembled, this technique is relatively complicated, time-consuming and expensive. There is also a chance that the parts do not perfectly mesh during the assembly, so that problems may arise at a later stage, when the plunger is pushed in the cylindrical body of the syringe or the like.

According to newer techniques, the two parts of the plunger are provided onto each other in a single injection-moulding machine, so that no separate mechanical mounting is required and the above-mentioned disadvantages are excluded.

A first example thereof is known from EP 1.099.449. The plunger body is hereby first injection-moulded out of hard plastic in a mould impression or cavity, after which a piston body made of a softer plastic is then formed on the plunger body by enlarging said mould impression near the front end of the formed plunger body and by then injecting the softer plastic in the space which has thus become available.

In order to be able to enlarge the above-mentioned mould impression, the mould is provided with a sliding part. A disadvantage of the use of such a sliding part consists in that a sub edge may be created on the front side of the formed piston body at the transition between said sliding part and the surrounding mould parts, which is undesirable in medical applications since, at the height of said sub edge, material particles may come off and thus end up in the reservoir of the syringe, and thus also in the medical liquid to be injected.

The injection of the plastic for forming the piston body is not simple either in this case. According to a first known possibility, the plastic may be injected laterally, which results in gate points being created in the side wall of the piston body, which is not desirable in practice. According to a second known possibility, the injection takes place through a supply duct formed in the plunger body. This prevents the formation of gate points on the front side or side wall of the piston body, but a disadvantage consists in that rather complex additional means are required to form such a supply duct through the plunger body.

A second example is known from U.S. Pat. No. 5,902,276, whereby a plunger body is formed in a first mould and a thin layer of soft plastic is subsequently provided in a second mould over the front end of said plunger body, in order to thus realise a piston body. The soft plastic is hereby injected via the back side of the piston body to be formed. However, a disadvantage hereby is that the presence of the already formed plunger body leaves little room to provide a nozzle in an efficient manner. Also, several nozzles per piston body have to be provided in order to make sure that the plastic spreads sufficiently through the mould impression. Also, the devices required to this end are relatively complex.

The present invention in general aims a method for manufacturing plungers for medical syringes out of plastic which is new and offers several advantages as such, such as for example an efficient manufacturing. Also, it aims a method which makes it possible to exclude the disadvantages of the above-mentioned known methods, at least when certain preferred embodiments are applied.

To this end, according to a first aspect, it concerns a method for manufacturing plungers for medical syringes, whereby such a plunger consists of at least two parts, namely a longitudinal plunger body made of plastic and a piston body provided at the front end of the plunger body which consists of a plastic which is softer than the plastic of the plunger body, characterised in that such a plunger is formed by first manufacturing the piston body and then the plunger body by means of injection moulding, whereby the plunger body is injected against the piston body.

Since, of each plunger the piston body is formed first, and then the plunger body, the liquid plastic for forming the plunger body is pressed against the supple plastic of the already formed piston body, as a result of which this supple plastic is pressed in somewhat elastically, so that a particularly tight fit of the piston body on the plunger body is obtained in the end.

By first forming the piston body and then the plunger body, this also offers the advantage that the plastic for the piston body can be easily provided via the side of the mould impression which is meant to form the back side of the piston body. In this manner, the formation of flash lines and gate points on the piston body can be easily excluded without any relatively complicated constructions for the supply of plastic being required. Hence, the piston body will preferably be formed such that its front side and side wall are entirely free of flash lines and/or gate points for the plastic.

In particular, the piston body is preferably formed in a mould impression whose walls, which connect to the front side and the side wall of the piston body to be formed, are part of one and the same undivided mould part.

The plastic for forming the piston body is preferably provided via the back side of the piston body to be formed in the mould impression concerned, possibly centrally, such that an even spread of the plastic in the mould impression is promoted. Moreover, a single nozzle may then be sufficient for the injection of said plastic.

As the piston body is formed first and this piston body consists of an elastically bendable material, this offers the advantage that the piston body, even when it has an inwardly directed collar and/or a part defining a counter draft, can be easily taken out of the mould, simply by pulling the mould part concerned loose, from behind said collar or out of the counter draft.

What precedes does not exclude, however, that according to another preferred embodiment, the piston body and the plunger body are connected to each other merely by the adhesion between the plastics out of which they are made, in particular without any parts meshing behind each other, counter drafts and the like thereby being realised. For, by making use of suitable plastics, for example the types of plastic mentioned hereafter, it is possible to obtain an adhesion which is sufficiently large without any explicit mechanical lock in the shape of meshing parts being required. This offers as an advantage that the mould for forming the piston body can be opened effortlessly, without the formed piston body coming out of the mould impression in an unwanted manner.

According to yet another possibility, use can also be made of a folding core, which makes it possible to form inwardly directed parts on the piston body. By folding the core before it is removed from the formed piston body, it can subsequently be removed from said piston body without any tensile force being exerted on the piston body.

According to the most preferred embodiment, the above-mentioned method is characterised in that the piston body is formed in a first mould impression, after which said piston body, while it is still being held in the first mould impression or a part thereof, is presented to a second mould impression in which the plunger body is then injected against the piston body by means of injection moulding, whereby mould impressions are applied having such a shape that the obtained plunger body and piston body are connected to one another thanks to their shape and/or thanks to the adhesion between the used plastics. By making use of two mould impressions instead of one mould impression which is locally enlarged after a first part has been moulded, this offers the advantage that the mould parts used thereby for forming the piston body and the plunger body respectively can be optimised individually.

Preferably, the method is also characterised in that, while a plunger body is being formed connected to a piston body, a subsequent piston body is formed simultaneously by means of the same nozzle with which the first piston body is realised, but in another mould impression. This allows for an efficient production whereby, during each injection cycle, a piston body as well as a plunger body are formed.

The piston body is preferably formed in a mould with mould parts whose partial surface mainly coincides with the back side of the piston body to be formed or extends parallel thereto. This makes it possible, after the piston body has been formed, to simply present the mould part in which the piston body is provided with the side defining the above-mentioned partial surface against the mould parts in which the plunger body is formed, without any complex movements of the mould parts being required.

The piston body is preferably made of a thermoplastic elastomer, while the plunger body is made of polypropylene or the like.

It should be noted that the invention also concerns embodiments whereby not the entire plunger body is injected against the piston body, but merely a part of this plunger body is injected against the piston body, after which the obtained part, formed of the aforesaid part and the piston body, are connected afterwards to a second, individually manufactured part of the plunger body, for example via a mechanical coupling between both parts. The above-mentioned part which is injected against the piston body is preferably made in the shape of an insert which makes it possible to make a connection to the rest of the plunger body at a later stage, as mentioned above. By an insert is meant that the above-mentioned part is only limited in size and has been mainly designed to form a connection with the piston body on the one hand, by means of embedment, and to form a part which can be easily connected to the rest of the plunger body as such on the other hand, for example by means of a mechanical coupling.

According to a special embodiment, when realising such a plunger or a part thereof, also an accessory is formed situated on the front side of the piston body, and which consists of a material which is different from the material of the piston body. Such an accessory can be of any nature whatsoever. A number of examples will be illustrated hereafter. As such an accessory is made of a separate material, this offers the advantage that its material selection can be optimised as a function of the purpose of such an accessory. The material of the accessory will preferably consist of a plastic which is harder than the plastic out of which the piston body is formed.

By an 'accessory which is situated on the front side of the piston body' is meant every part which is accessible via the front side of the piston body.

According to a first possibility, the above-mentioned accessory consists of a part which extends frontally from the front side of the piston body and which, when the plunger is situated in the syringe, can at least partially penetrate in the outlet of the syringe, which makes it possible to optimally empty the syringe. The use of such a protruding part is known as such, but not that it is made of a different material, in particular another plastic than the one out of which the piston body is formed. By making use of different materials is thus obtained that independent material selections can be made whereby, when the material of the piston body is selected, an optimisation of the sealing can be aimed at, whereas when the material of the protruding part is selected, an optimisation can be aimed at for this part in order to make it function optimally. Thus, for example, by selecting a harder plastic, the protruding part can be made rather rigid, as a result of which it cannot bend and will not be situated exactly in front of the outlet.

According to another possibility, the above-mentioned accessory consists of a part which makes it possible to create a passage between the front side and the rear side of the piston body when emptying the syringe, in order to prevent the syringe being re-used, as a result of which what is called a safety syringe is obtained.

The above-mentioned accessory is preferably made in one of the following shapes:
  as a part which is made in one piece with the plunger body or a part thereof, and which is thus formed simultaneously with the latter during the injection moulding, which offers the advantage that the accessory always remains perfectly aligned, for example remains axially aligned, and that no separate injection moulding cycle is required to form the accessory;
  as a separate part provided on the front side of the piston body;
  as a separate part provided on the front side of the piston body, whereby this part is injected against the material of the piston body after the piston body has been formed, which offers the advantage that no liquid can leak away between both plastics.

It should be noted that the invention can also be used for realising short plungers, in particular plungers of the type designed to co-operate with a drive element. In practice, such plungers are used for example in syringes or the like to slowly administer medical substances to a patient, in a dosed manner by means of a pump. Such a syringe is then connected to the patient via a catheter. The plunger is connected to an automatically driven drive element of the pump, which moves very slowly when in use.

Also, taking into account what precedes, the present invention, according to a second aspect, provides for a method as described above, characterised in that, instead of being used to manufacture plungers with a longitudinal plunger body, it is used to manufacture plungers of the type which is meant to be used in combination with a drive element, whereby such a plunger then mainly consists of a piston body and a plunger part, whereby this plunger part is fit to co-operate with such a drive element.

It should also be noted that the characteristic in that a part is formed at the height of the piston body which protrudes frontally from the front side of the piston body and which, when the plunger is situated in the syringe, can penetrate at least partially in the outlet of the syringe, whereby this part and the piston body are formed of materials, in particular plastics which are injected against one another, is advantageous when the piston body is moulded first and then the protruding part, as well as when the protruding part is moulded first and then the piston body. For, in both cases, the above-mentioned advantages remain applicable.

Taking into account what precedes, the present invention, according to a third aspect, also provides for a method for manufacturing plungers for medical syringes comprising at least a piston body, characterised in that, at the piston body, a part is formed which protrudes frontally from the front side of the piston body, and which, when the plunger is situated in the syringe, can penetrate at least partially in the outlet of the syringe, whereby this part is formed of a material which differs from, and is preferably harder than the material of the piston body, and whereby the piston body on the one hand and said protruding part on the other hand are injected against one another, whereby the above-mentioned part is either or not made in one piece with a plunger body belonging to the plunger.

According to a fourth aspect, the invention concerns a device for the application of the method according to the first and second aspect, characterised in that it at least consists of a number of mould parts which at least define a first mould impression and a second mould impression to form the above-mentioned piston body and the above-mentioned plunger body respectively, or a part of this plunger body; a motion mechanism which makes it possible to move the above-mentioned mould parts in relation to one another and to position them differently so that, in a first position, a piston body can be injected, whereas in a second position, the plunger body or the aforesaid part thereof can be injected against the piston body; and injection means to supply the plastic to be injected to the aforesaid mould impressions respectively.

According to the invention, the present device may have some more special additional characteristics, as explained in the following description and as described in the accompanying claims, which characteristics can be either or not combined.

It is clear that also devices which make it possible to realise the methods according to the aforesaid third aspect fall within the scope of the invention. Its construction, taking the description of the method as a basis, lies within the scope of the knowledge of any craftsman.

Naturally, the invention also concerns plungers, as well as parts of plungers, made according to the preceding method, as well as syringes that are equipped with such plungers.

Finally, it should be noted that also the fact that the above-mentioned part protruding from the piston body consists of another material than the piston body itself, is advantageous as such and offers several of the above-mentioned advantages, irrespective of whether this part has been formed by forming it together with the piston body in two successive injection moulding cycles, or in any other way whatsoever, for example made separately to be subsequently connected to the piston body in a mechanical manner.

Taking into account what precedes, the invention also concerns a syringe for medical purposes, according to a fifth aspect, comprising at least a cylinder body with an outlet which is formed of a narrowed outlet part, as well as a plunger working in conjunction with the cylinder body which is provided with a piston body and a plunger body, characterised in that the plunger comprises a part which protrudes frontally from the front side of the piston body and which can penetrate at least partially in the above-mentioned outlet part, whereby this part is formed of a material which is different from the material of the piston body, and preferably consists of a plastic which is harder than the material out of which the piston body is formed.

In this case also, the part which protrudes frontally from the front side of the piston body, can be made according to either of the following two possibilities:
- as a part which is made in one piece with the plunger body or made in one piece with a part of this plunger body;
- as a separate part provided at the piston body.

In order to better explain the characteristics of the invention, the following preferred embodiments are described as an example only without being limitative in any way, with reference to the accompanying drawings, in which:

FIG. 1 represents a syringe which is equipped with a plunger made according to the method of the invention;

FIG. 2 represents the plunger of the syringe from FIG. 1 in perspective;

FIG. 3 represents a section according to line III-III in FIG. 2;

FIGS. 4 to 8 represent a device according to the invention in different stages of the method;

Figure 11:
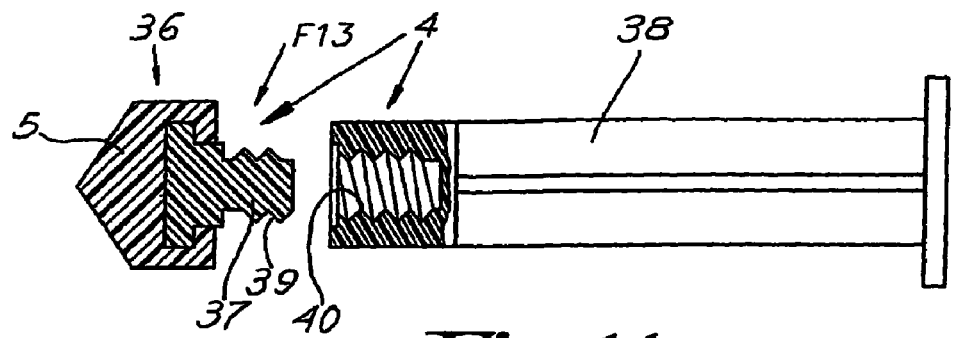
FIGS. 11 and 12 represent a plunger body as dismounted and as mounted respectively, which has been realised according to a method of the invention.
Figure 13:
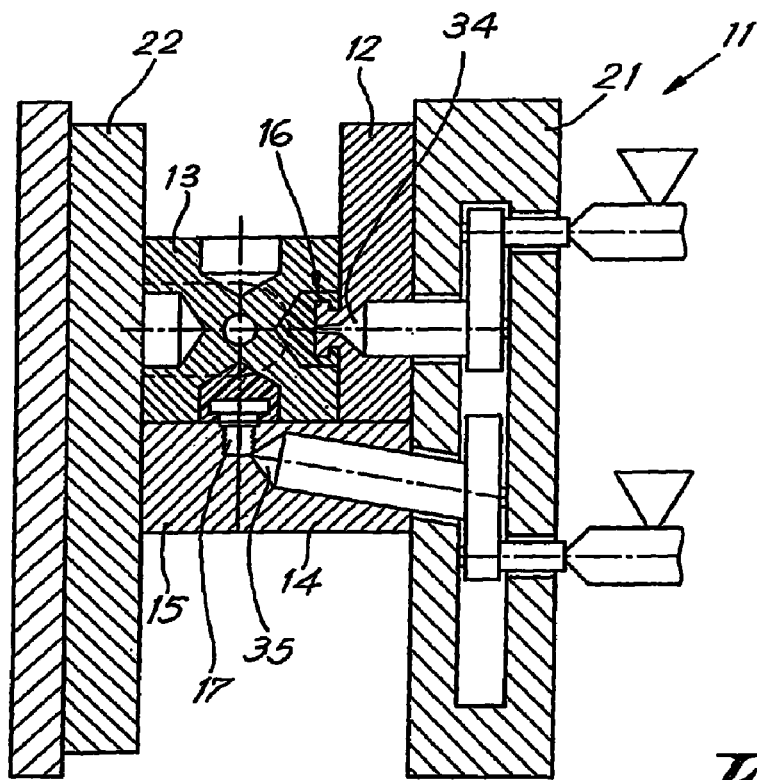
Figure 14:
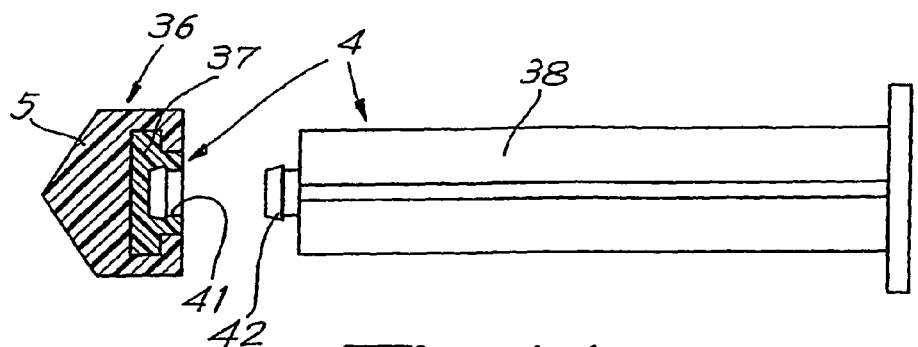
Figure 15:
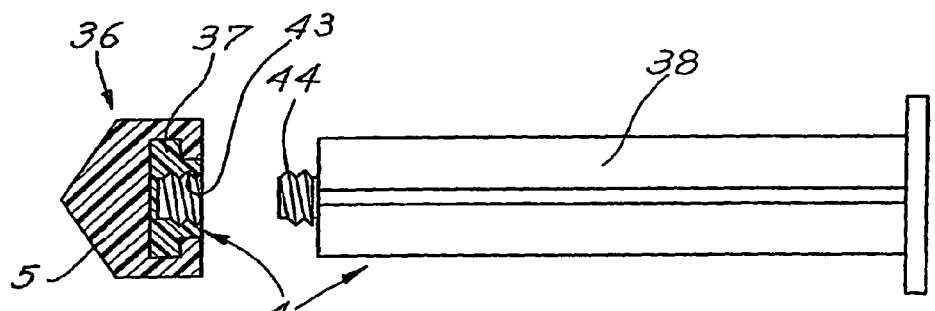
Figure 16:
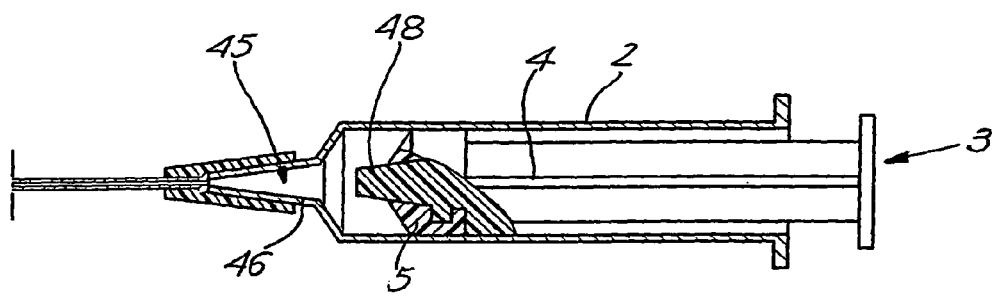
Figure 17:
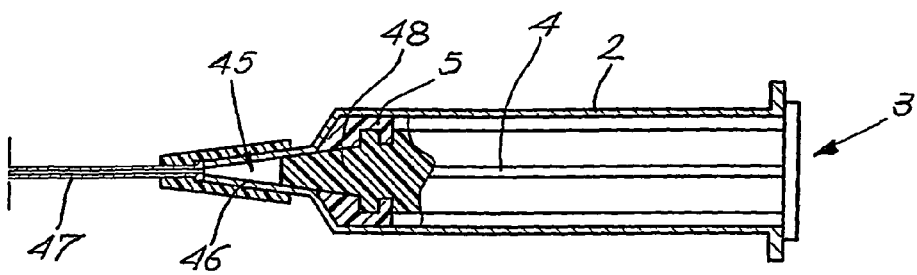
Figure 18:
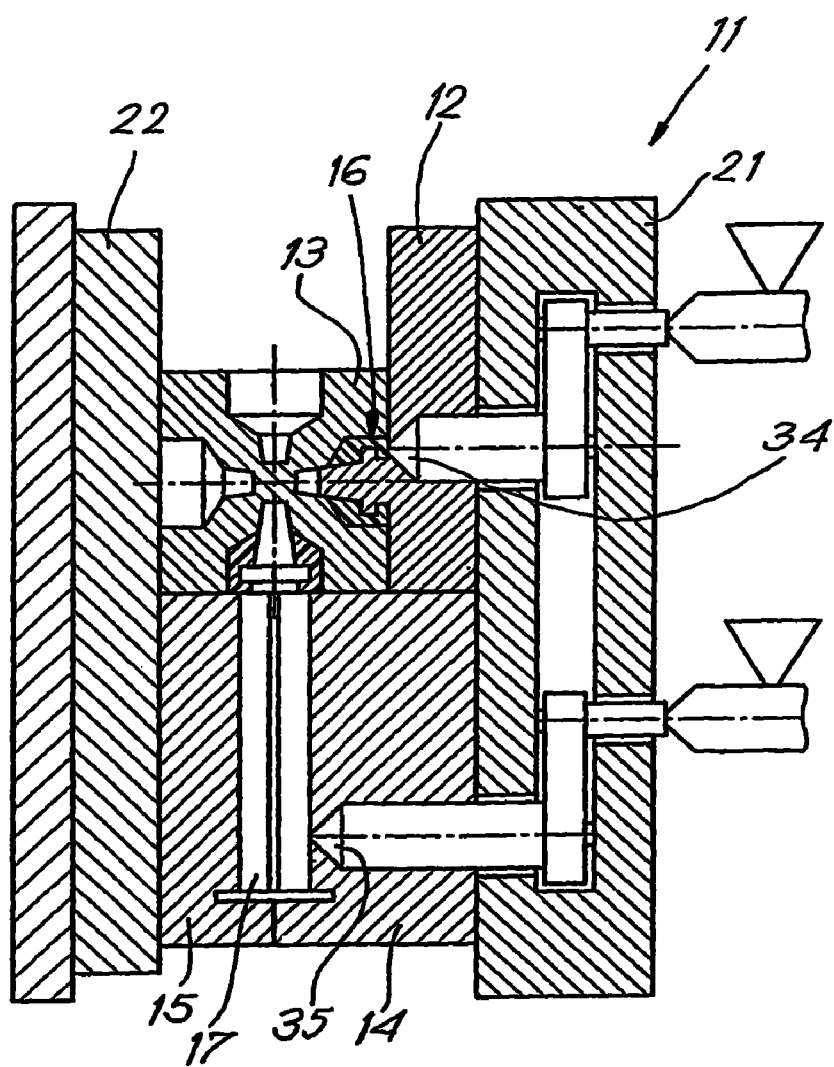
Figure 19:
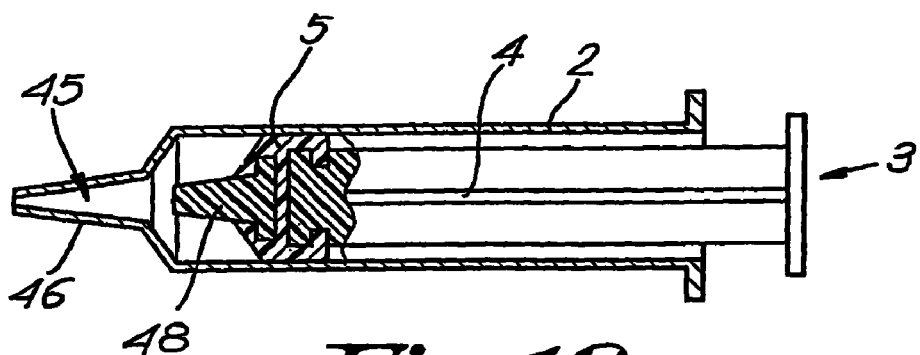

FIG. 13 schematically represents how the part which is indicated by F13 in FIG. 11 can be realised by means of successive injection mounting cycles;

FIGS. 14 and 15 represent two variants of a plunger body according to the invention, for a view similar to that in FIG. 11;

FIGS. 16 and 17 represent a section of a syringe according to the invention, for two different positions of the plunger body;

FIG. 18 shows how the plunger bodies for forming syringes according to FIGS. 16 and 17 can be formed by successive injection moulding cycles;

FIG. 19 shows another special embodiment of a syringe according to the invention.

A plastic syringe 1, as is used for medical applications, mainly consists, as is represented in FIG. 1, of a recipient, in this case a cylinder 2 and a plunger 3.

As is represented in greater detail in FIGS. 2 and 3, the plunger 3 is composed of a plunger body 4 and a piston body 5, which in the given embodiment have such a shape that they mesh and as such remain coupled.

As is represented, the plunger body 4, which normally consists of a relatively hard plastic, for example polypropylene, preferably has a cross-shaped shaft 6 provided with a collar 7 on one far end.

The above-mentioned piston body 5, which is preferably made of a soft material, such as thermoplastic elastomer, is made in the shape of a head and is provided with an excavation 9 on the rear side 8, which is partially confined by an inwardly directed collar 10, which co-operates with the collar 7 of the plunger body 4.

The invention aims a method and a device for manufacturing plungers 3, or at least plungers of a similar type, in other words plungers 3 which consist of a plunger body 4 and a piston body 5 of different plastics. In order to illustrate the method, the construction of a preferred embodiment of a device 11 applied thereby, in particular a combined injection mould, is first described hereafter by means of FIGS. 4 to 8.

The device 11 comprises a number of mould parts, in this case four, 12-13-14-15 respectively, defining 'first' mould impressions 16 and a 'second' mould impression 17, for forming a first part of the plunger 3, namely the piston body 5, and a second part of the plunger 3, namely the plunger body 4 respectively.

The mould parts 12-13-14-15 together form three parts 18-19-20 which can be mutually moved.

The first part 18 is formed of the mould parts 12 and 14 which are mounted on a common support 21 which is preferably fixed.

The second part 19 is formed of the mould part 15 which is mounted on a support 22. This second part 19 can make a translation movement T1 in relation to the first part 18.

The third part 20 is formed of the mould part 13, which is mainly square and movable, in particular is provided in an extending and rotatable manner on the support 22.

The first mould impressions 16 are formed of cavities 23A-23B-23C-23D provided on the surface of the mould part 13, in this case on each of the four sides thereof respectively, as well as of the wall part 24 of the mould part 12 with which the cavity which is turned towards this wall part 24 can be sealed. On the wall part 24 is provided a protruding part 25 which is designed to form the excavation 9, and which is provided with a recess 25A which is confined by a collar 25B.

Hereby is obtained that the partial surface between the mould parts 12 and 13 coincides with the rear side 8 of the piston body 5 to be formed.

By means of the translation movement T1, the mould impression 16 can be opened, sealed respectively.

The second mould impression 17 is mainly formed of the cavities 26 and 27 provided in the surface of the mould parts 14 and 15 respectively. These cavities 26 and 27 hereby open into sides 28 and 29, as well as into sides 30 and 31 standing at right angles thereto.

Further, these cavities 26 and 27 are situated such that the mould impression 17 formed thereby, when the whole is closed, connects to the cavity 23B. The longitudinal axes of the mould impression 17 and the mould impression 16, in particular the cavity 23B, are hereby situated in each other's prolongation.

The mould parts 14 and 15 can also be moved towards one another and away from one another by means of the translation movement T1. Further, the mould part 13 can make a translation movement T2 as well as a rotational movement R.

In order to realise the movements T1, T2 and R, the device 11 is provided with a motion mechanism, consisting of drives which can move the three parts 18-19-20 in relation to one another, as will be further described, which are not represented for clarity's sake. It should be noted that the mould part 13 can also make a translation movement T3 in relation to the support 22 which has to make it possible for the mould part 13 to freely rotate.

For the rotation, use is made of a rotating indexing mechanism 32, whose axis of rotation 33 has a direction which is different from the direction or directions of movement according to which the mould parts 12-13 and 14-15 open and close.

It should be noted that, as represented in the figures, the mould parts 12-13-14-15 together define three partial surfaces, in other words surfaces whose composed mould opens and closes, which are situated in a stepped manner in relation to one another. This stepped construction allows for a compact construction.

Further, the device 11 comprises injection means for supplying the plastic to be injected to the aforesaid mould impressions respectively which consist of nozzles 34-35 provided in the fixed part 18 and which preferably have parallel longitudinal axes, and which also open in parallel partial surfaces.

Moreover, the nozzle 34 extends centrally through the protruding part 25.

The working of the device 11, as well as the accompanying method, is described hereafter by means of the different positions represented in FIGS. 4 to 8.

FIG. 4 shows the composed mould when closed. A first plastic is hereby provided in the first mould impression 16 via the nozzle 34, in particular the cavity 23A. In the cavity 23B, a piston body 5 formed during a preceding cycle is already present.

In the second mould impression 17 is simultaneously injected a second plastic via the nozzle 35, whereby this plastic not only fills the cavities 26 and 27, but also the excavation 9 of the piston body 5 which is presented against it and which is present in the cavity 23B.

Figure 5:
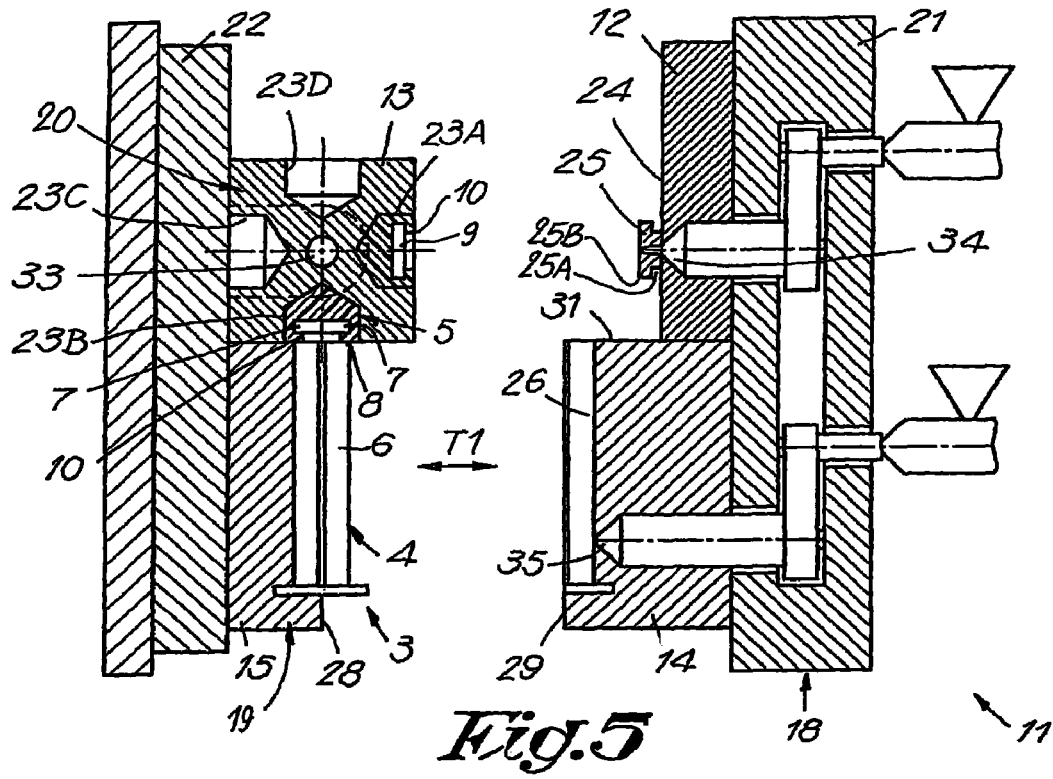

After the piston body 5 in the mould impression 16 and the plunger body 4 in the mould impression 17 have cured sufficiently, the mould is opened according to the direction T1, as represented in FIG. 5, whereby the protruding part 25 of the mould part 12 is pulled out of the excavation 9 of the piston body 5, while the latter is retained in a manner which is not represented in the figures. As the piston body 5 is made of supple plastic and is elastically bendable, the protruding part 25 can be pulled loose with its edge 25B from behind the supple edge 10 without any problem.

Possibly, means which are not represented can be provided which hold the piston body 5 in the mould part 13 while the part 25 is being pulled out of the excavation 9, in order to prevent the piston body 5 from coming out of the mould part 13 as well. Further, use can be made of a folding core 25, either or not combined with such means, such that when the mould concerned is opened, no or practically no tensile forces will be exerted on the piston body 5.

Figure 6:
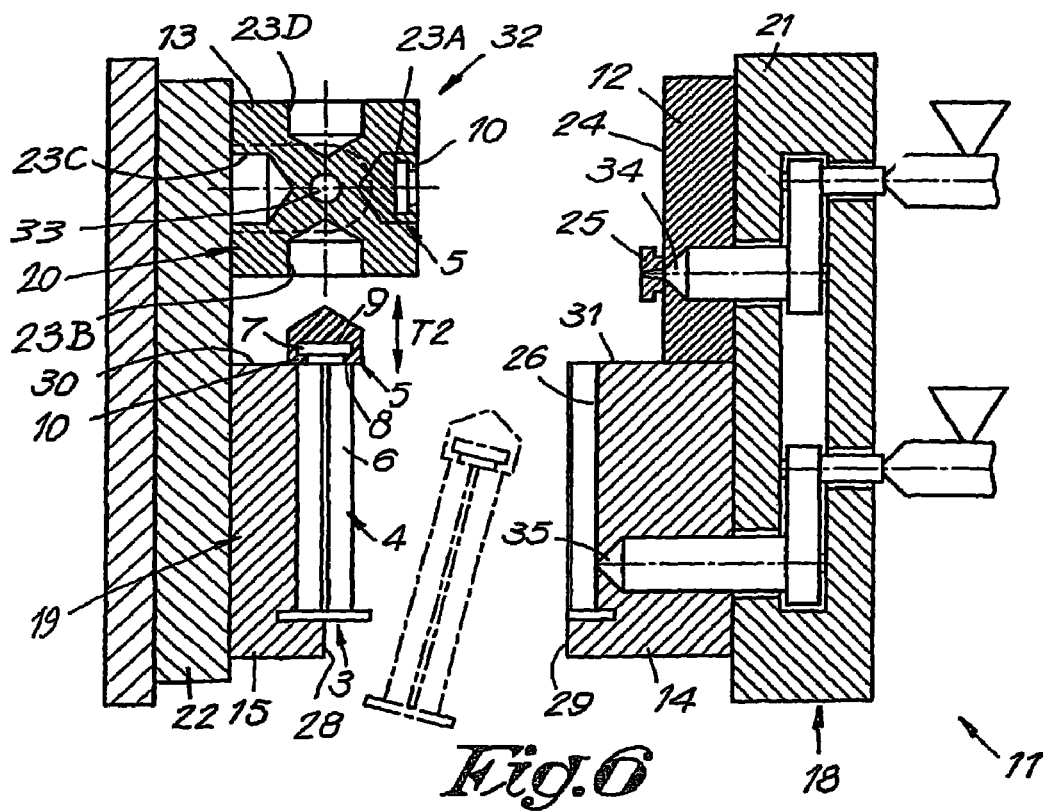

FIG. 6 shows how the mould part 13 is moved according to arrow T2, namely parallel to the support 22, as a result of which the piston body 5 is pulled out of the cavity 23B of the mould part 13, as this piston body 5 is stuck behind the collar 7 of the plunger body 4 with its collar 10.

Figure 7:
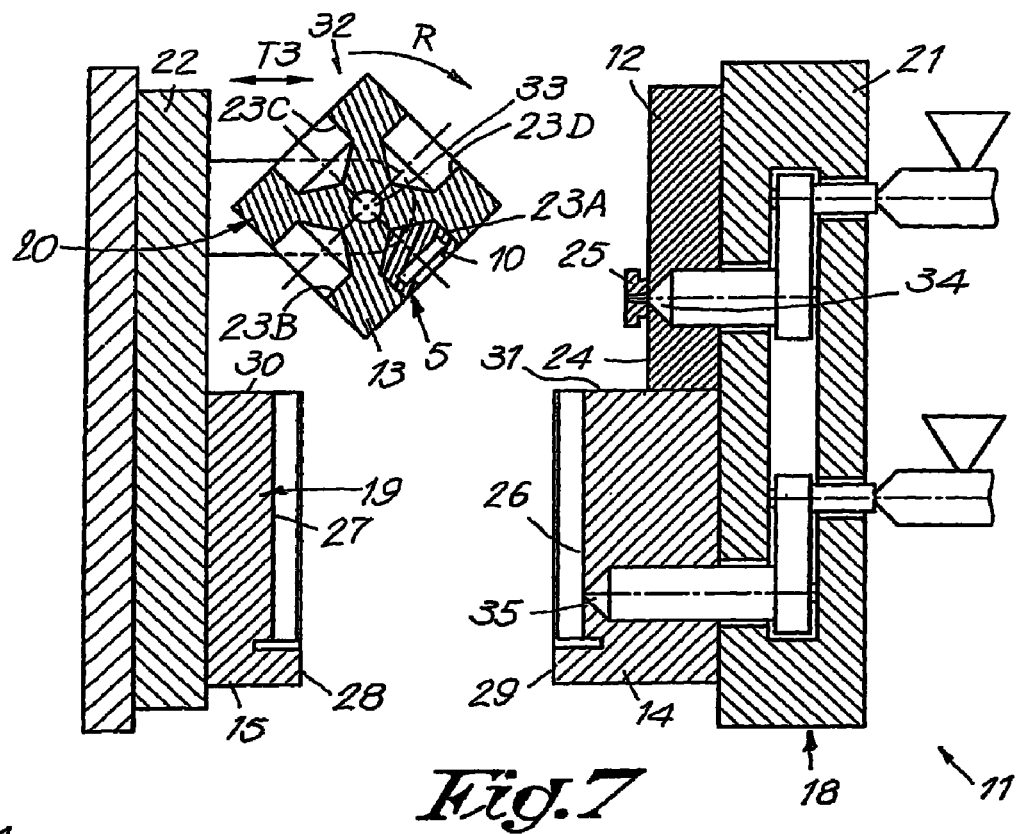

After the plunger 3 has been ejected from the mould, as represented by means of a dot and dash line in FIG. 6, the mould part 13 is pulled out according to arrow T3 and then rotated over 90° in the sense of rotation R by means of the indexing mechanism 32, as represented in FIG. 7.

Figure 8:
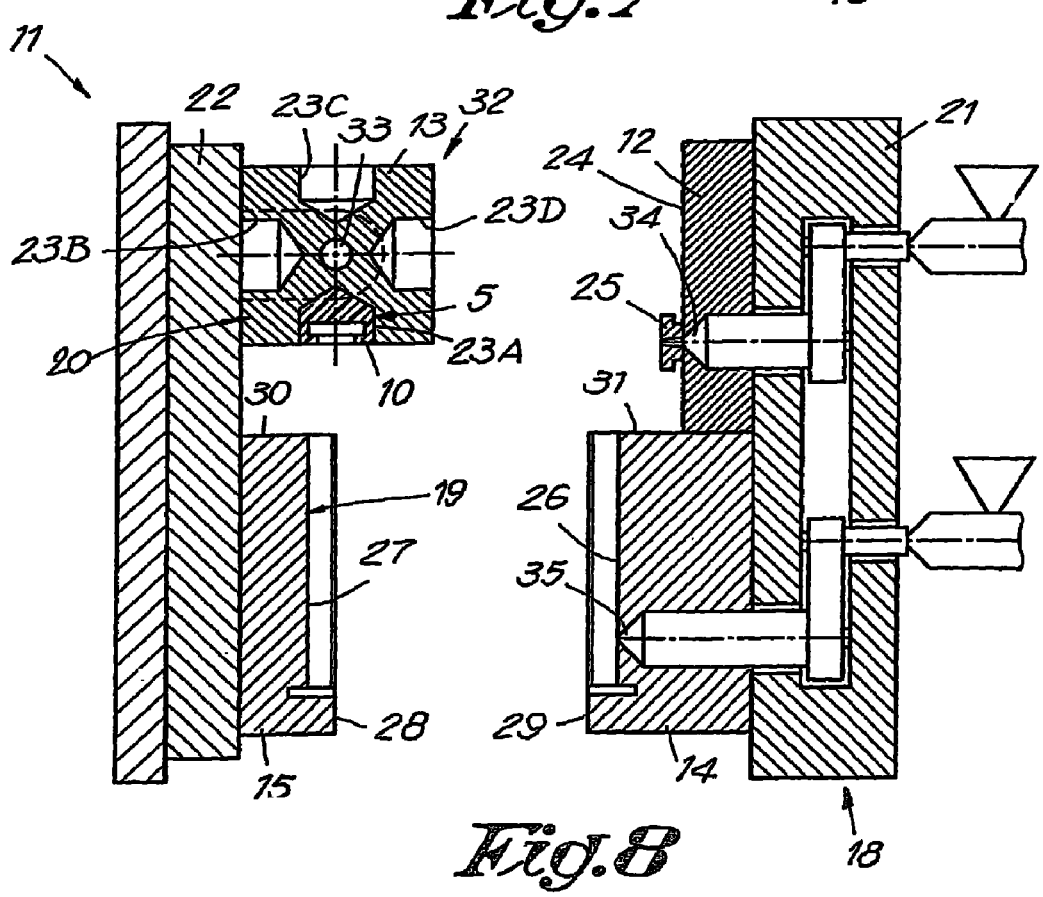

FIG. 8 shows the composed mould after the mould part 13 has first been provided against the support 22 according to arrow T3.

Finally, the mould is closed again according to arrows T2 and T1, after which a new piston body 5 and a new plunger body 4 are formed, in the mould impressions 16 and 17 respectively, by injecting plastic.

Figure 9:
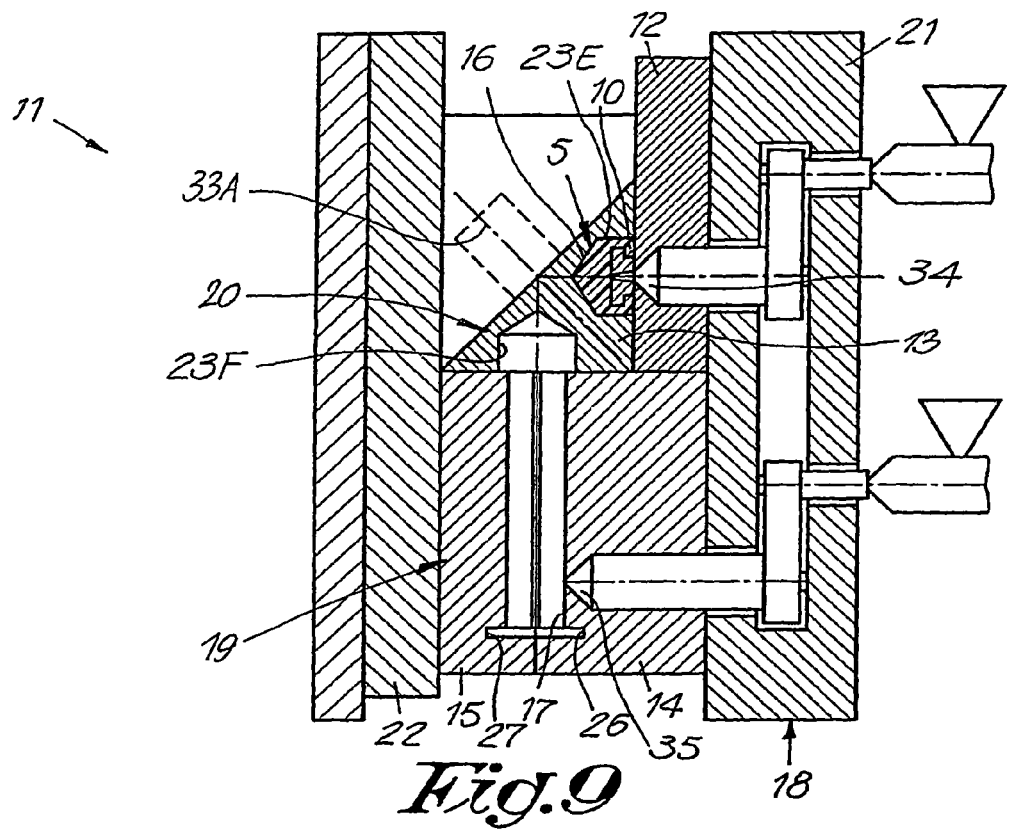
FIGS. 9 and 10 represent a variant of the embodiment of a device according to the invention, when closed and when opened respectively.
Figure 10:
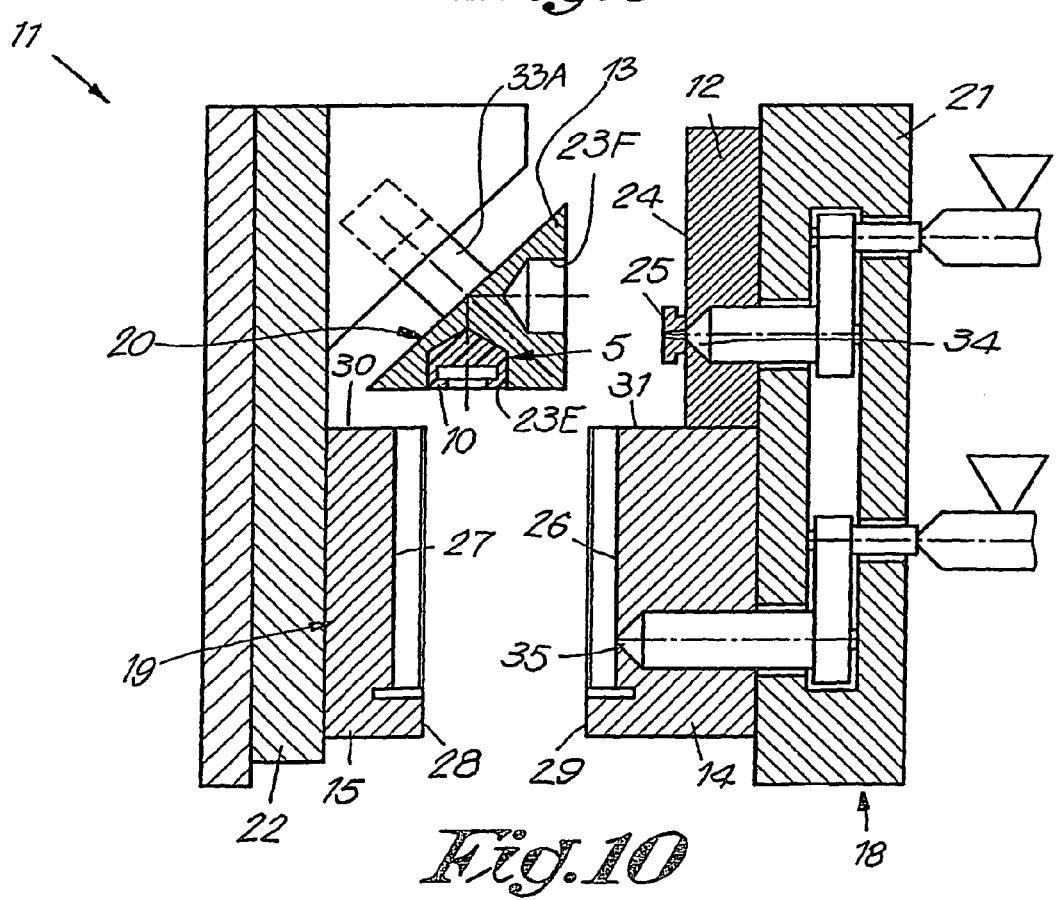

FIGS. 9 and 10 represent a second preferred embodiment of the device according to the invention, whereby the second mould part 13 has two cavities 23E and 23F, and this mould part 13 can be rotated along a tilted shaft 33A which extends at an angle of 45° in relation to the longitudinal axes of the cavities 23E and 23F.

The use and working of this embodiment is analogous to that of the first embodiment, with as a sole difference that the mould part 13 is rotated in another manner.

It is clear that in both embodiments, the leading idea of the method of the invention is applied, i.e. that a piston body 5 is injected first, and that the plunger body 4 is subsequently injected against the latter.

As represented, the piston body 5 and the plunger body 4 are preferably formed in one and the same direction. It is clear, however, that this does not exclude that, according to a variant, the piston bodies 5 could be formed in a first device, could be removed from this device and then be provided in a second device to there inject the plunger body 4 against it.

In order to keep the formed piston bodies 5 with some resisting force in the mould impression 16 concerned, the side walls can possibly be made with a light counter draft.

Instead of forming a connection with parts meshing behind one another, such as the collars 7 and 10, it is also possible to mainly or even exclusively base the connection on the adhesive force between both plastics. In this case, it is possible to work with a simple excavation 9 in the piston body 5, which has no inwardly directed part, and the plunger body 4 can be simply made with a part reaching into the excavation 9.

As mentioned in the introduction, the invention also concerns embodiments whereby only a part of the plunger 3 is formed in the above-mentioned injection moulding cycles, in particular a part 36 which, as represented in FIG. 11, consists of the piston body 5 and a part 37 of the plunger body 4, whereby this part 37 has the shape of an insert and is made such that it can be coupled to a second part 38 of the plunger body 4 to be produced separately.

Figure 12:
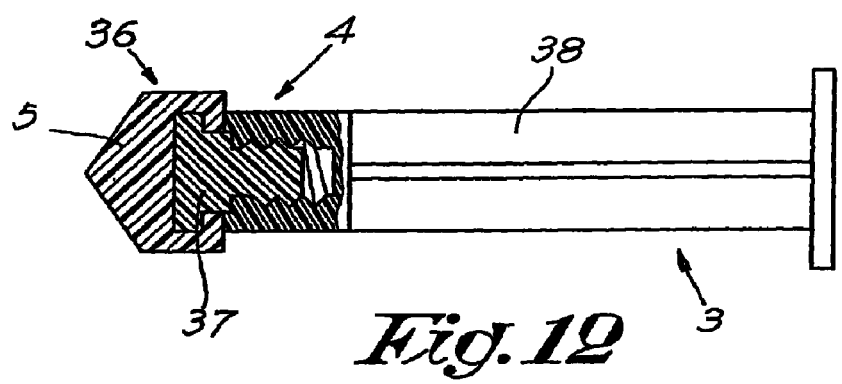

The parts 37 and 38 hereby comprise coupling means which make it possible for these parts to be connected. In the embodiment of FIG. 1, these coupling means are formed of threaded parts 39 and 40, which make it possible for the parts 37 and 38 to be connected, as represented in FIG. 12.

FIG. 13 shows that the part 36 can be realised in an almost similar manner as the plungers 3 in the device 11 of FIG. 4. The only difference consists in that the shape of the mould parts concerned have to be adjusted to the shape of the part 37 instead of to the shape of the entire plunger body 4.

FIG. 13 shows, consistent with FIG. 4, a device 11 in which the piston body 5 is each time injected first, and subsequently the accompanying part 37.

The above-mentioned coupling means between the parts 37 and 38 can be made in different shapes. FIG. 14, for example, shows a variant with coupling parts 41-42 which allow for a snap-in connection. FIG. 15 shows a variant whereby the part 37 is provided with a threaded part 43 with internal screw thread, and the part 38 is provided with a threaded part 44 with outside thread.

FIGS. 16 and 17 represent a special embodiment of a syringe 1 for medical purposes according to the invention. This syringe 1 comprises at least a cylinder body or a cylinder 2 with an outlet 45 which is mainly formed of a narrowed outlet part 46 onto which can be fixed, for example, a hollow needle 47 or a catheter which is not represented, as well as a plunger 3 working in conjunction with the cylinder body 2 which is provided with a plunger body 4 and a piston body 5. What is special hereby is that the plunger 3 has an accessory, in this case a part 48 which protrudes frontally from the front side of the piston body 5 and which, as represented in FIG. 17, can penetrate at least partially in the above-mentioned outlet part 46, whereby this part 48 is formed of a material which differs from the material of the piston body 5, and which preferably consists of a plastic which is harder than the material out of which the piston body 5 is formed.

In the example of FIGS. 16 and 17, the part 48 is made in one piece with the plunger body 4. According to a variant which is not represented, it could also be made in one piece with a part 37 in the shape of a insert.

The part 48 makes it possible to restrict the amount of liquid which remains in the syringe 1 when the syringe is used, after the plunger 3 has been entirely pressed in, to a minimum, which is of major importance in the case of very expensive medical preparations.

FIG. 18 represents a device 11 with which the plungers 3 of the syringes 1 in FIGS. 16-17 can be realised, for example, which device, except for the use of mould parts which are shaped differently, corresponds to the device from FIG. 4.

FIG. 19 shows a variant whereby the plunger 3 has a part 48 which is fixed in the piston body 5 as a separate element.

As mentioned in the introduction, the use of a part 48 which consists of a material which is different from the material of the piston body 5 offers several advantages.

As further mentioned in the introduction, the invention is not restricted to a specific technique for applying the part 48 to the plunger 3.

In the case of a safety syringe of the type mentioned in the introduction, the accessory referred to will then be made analogous to what is seen in FIG. 16, for example, with this difference that the protruding part 48 is hollow and that its excavation is connected to the compartment of the cylinder 2 in which the plunger body 4 is situated. Further, a pointed part, a knife or the like, is then for example provided in the outlet part 46 in this case, such that when the syringe is pressed in, an opening is made through the hollow part, as a result of which the syringe becomes unserviceable. According to a variant, the hollow part which can be pricked through or cut through, can also be made as a part which is level to the front side of the piston body or which is somewhat countersunk in it, instead of being made as a protruding part.

The invention is by no means limited to the above-described embodiments given as an example and represented in the accompanying drawings; on the contrary, the above-mentioned method as well as the devices applying the method according to the invention, and further also the claimed embodiments for syringes, can be made in all sorts of variants while still remaining within the scope of the invention.

Thus, for example, the invention is applicable to all sorts of syringes which can be used for medical purposes, whereby injection syringes as well as dose syringes may be concerned. Although the invention is in the first place meant for smaller syringes to be operated manually, this does not exclude that it can also be used for the production of larger syringes, for example of 50 ml, which are used, as is known, to very slowly administer an infusion to a patient, whereby the plunger is pressed in very slowly and steadily by means of a drive element.

The invention claimed is:

1. Method for manufacturing plungers for medical syringes, said plunger comprising at least two parts including a longitudinal plunger body made of plastic and a piston body provided at a front end of the plunger body, which piston body comprises a plastic which is softer than the plastic of the plunger body, wherein said plunger, or at least a part of the plunger, is formed by first manufacturing the piston body and then the plunger body, or at least a part of the plunger body, by means of injection moulding, and wherein the plunger body, or said part of the plunger body, is injected against the piston body, said piston body having a front side and a side wall and being formed such that the front side and side wall thereof are free of any flash lines and/or gate points for the plastic.

2. Method according to claim 1, wherein the piston body and the plunger body, or said part of the plunger body, are connected solely by the adhesion between the plastics out of which they are made, without any meshing parts or counter drafts being formed thereby.

3. Method according to claim 1, wherein at least one inwardly directed part defining a counter draft is formed on the piston body, and use is made during the injection moulding of a mould part having a protruding part in which one or several lateral recesses are provided forming a counter draft, such that the mould part may be removed from the piston body due to the elastic flexibility of the material of the piston body, to thereby enable the protruding part to be pulled from the formed piston body.

4. Method according to claim 1, wherein the plastic forming the piston body is provided in a respective mould cavity via a back side of the piston body to be formed.

5. Method according to claim 1, wherein the piston body is formed in a first mould cavity, after which the piston body, while it is still held in a first mould cavity or a part thereof, is presented to a second mould cavity in which the plunger body, or the part of the plunger body, is then injected against the piston body by means of injection moulding, and wherein mould cavities are used having such a shape that the resulting plunger body or the part of the plunger body, and the piston body are connected to each other due to their shape and/or adhesion between the plastics.

6. Method according to claim 5, wherein while the plunger body or the plunger body part is formed such that it connects to the piston body, a subsequent piston body is simultaneously being formed by means of a connector nozzle with which the first piston body is formed, but in another mould cavity.

7. Method according to claim 1, wherein the piston body is formed in a mould with mould parts whose partial surface mainly coincides with a rear side of the piston body to be formed or extends parallel thereto, after which a mould part with the piston body provided in it is presented against other mould parts in which the plunger body or the part of the plunger body is formed.

8. Method according to claim 1, wherein when forming the plunger or a part of the plunger, an accessory is also formed which is located with at least a part thereof on the front side of the piston body, and which comprises a material which is different from the material of the piston body.

9. Method according to claim 8, wherein the material of the accessory comprises a plastic which is harder than the plastic out of which the piston body is formed.

10. Method according to claim 8, wherein accessory comprises a part which extends frontally from the front side of the piston body and which, when the plunger is situated in the syringe, can at least partially penetrate in an outlet of the syringe, in order to be able to optimally empty the syringe.

11. Method according to claim 8, wherein the accessory comprises a part which enables creation of a passage between the front side and a rear side of the piston body when emptying the syringe in order to prevent the syringe from being re-used.

12. Method according to claim 8, wherein the accessory can be made in a shape selected from the following shapes:
as a part made in one piece with the plunger body or said part of the plunger body, and thus formed simultaneously with the plunger body or part thereof during the injection moulding;
as a separate part provided on the front side of the piston body;
as a separate part provided on the front side of the piston body, wherein such separate part is injected against the material of the piston body after the piston body has been formed.

13. Method according to claim 1 wherein, in the case where only a part of the plunger body is injected against the piston body, such plunger body part is made as an insert, whereby it is possible to provide for a connection with the rest of the plunger body at a later stage.

14. Method according to claim 1, wherein, instead of being used for manufacturing plungers with a longitudinal plunger body the method is used for manufacturing plungers of the type intended to be used in combination with a drive element, wherein each such plunger then comprises a piston body and a plunger part, such that the plunger part is configured to co-operate with such drive element.

15. Method for manufacturing plungers for medical syringes having at least a piston body comprising forming a part of the piston body at the location of the piston body which protrudes frontally from a front side of the piston body and which, when the plunger is located in a syringe, can penetrate at least partially through an outlet of the syringe, wherein said piston body part is formed of a material which is different from the material of the piston body, and wherein the materials forming the piston body on the one hand and the aforesaid protruding part on the other hand are injected against one another such that said piston body be is made in one piece with a plunger body belonging to the plunger.

* * * * *